United States Patent
Ishikawa et al.

(10) Patent No.: US 6,266,567 B1
(45) Date of Patent: Jul. 24, 2001

(54) IMPLANTABLE EPICARDIAL ELECTRODE

(75) Inventors: Akira Ishikawa, Royce City; Nabuo Takeda, Richardson; Suzanne I. Ahn, Dallas; Steven R. Hays, Dallas, all of TX (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/323,585

(22) Filed: Jun. 1, 1999

(51) Int. Cl.[7] ................................ A61N 1/375
(52) U.S. Cl. .................. 607/36; 607/132; 607/33
(58) Field of Search ............... 607/119, 129–132, 607/33, 36, 60, 61; 600/374, 375

(56) References Cited

U.S. PATENT DOCUMENTS

| | | | |
|---|---|---|---|
| 4,256,115 | * | 3/1981 | Bilitch ............................. 607/0.36 |
| 5,312,439 | * | 5/1994 | Loeb ................................ 607/2 |
| 5,405,367 | * | 4/1995 | Schulman et al. ............... 607/61 |
| 5,725,559 | * | 3/1998 | Alt et al. .......................... 607/5 |
| 5,792,208 | * | 8/1998 | Gray ................................ 607/36 |

* cited by examiner

Primary Examiner—Jeffrey R. Jastrzab
(74) Attorney, Agent, or Firm—Howison, Chauza, Thoma, Handley & Arnott, L.L.P.

(57) ABSTRACT

An implantable epicardial lead (13) is provided which is comprised of two spherical ICs (25) and (26) disposed at opposite ends of a supporting structure and separated by a predetermined distance. These spherical ICs comprise an anode and a cathode, each having connections thereto. The epicardial lead (13) includes circuitry for allowing inductive coupling of power into the epicardial lead (13) for storage in a capacitor (926). A switch (928) allows for selective discharge of the capacitor (926) to the surrounding myocardium into which it is implanted. The epicardial lead (13) also includes a receive/transmit device (942) for receiving command information for storage in a memory (939) to provide operation information therefor and also for receiving sensed information therefrom. The sensed information is sent via a switch (930).

38 Claims, 8 Drawing Sheets

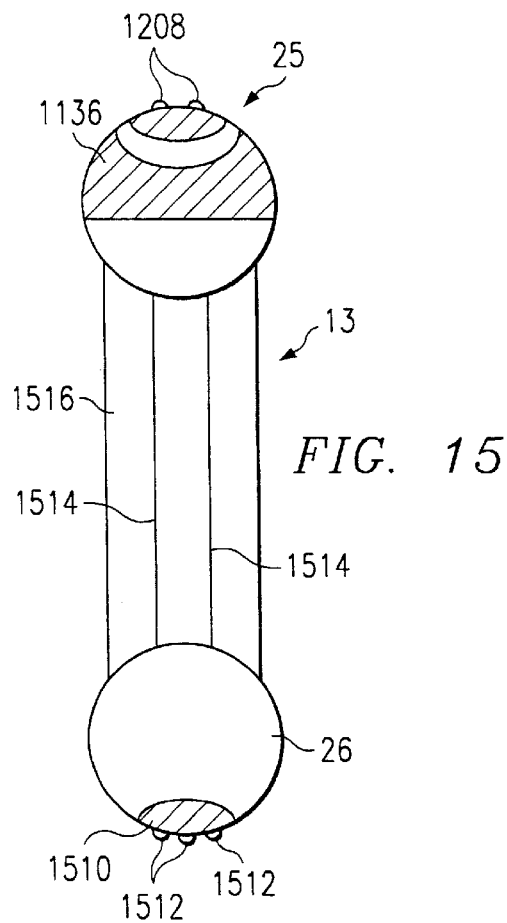
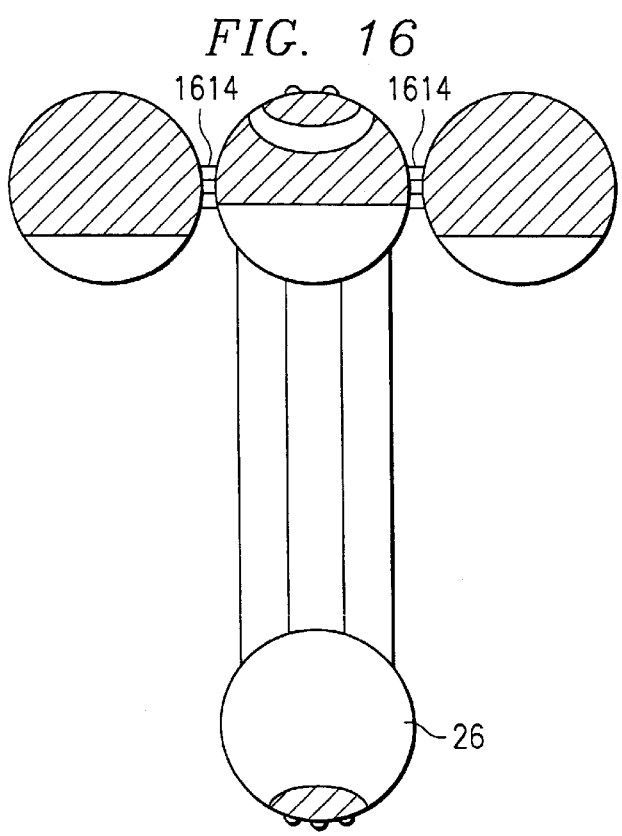
FIG. 15
FIG. 16
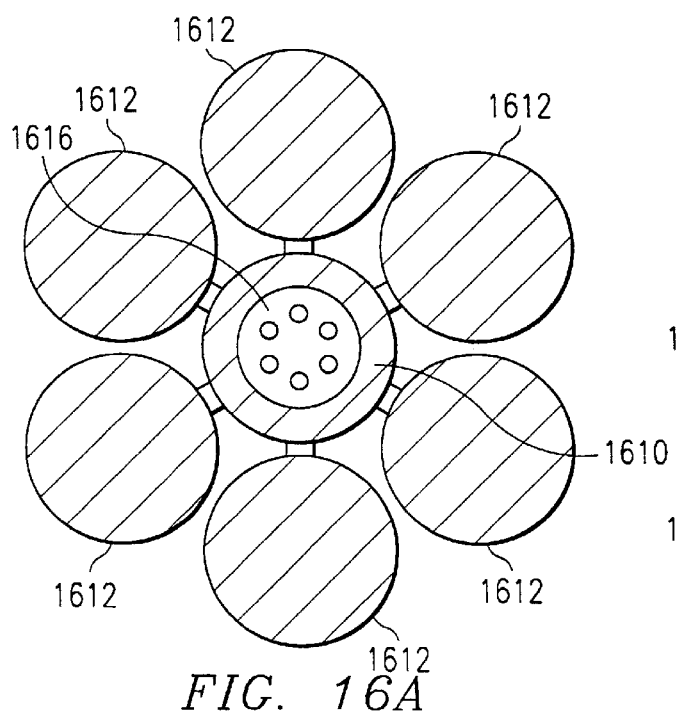
FIG. 16A
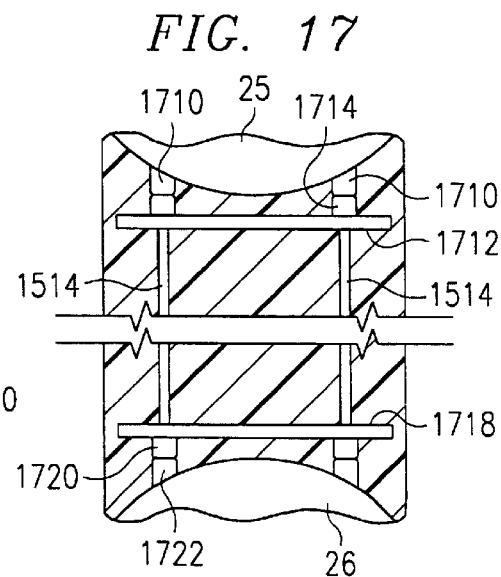
FIG. 17

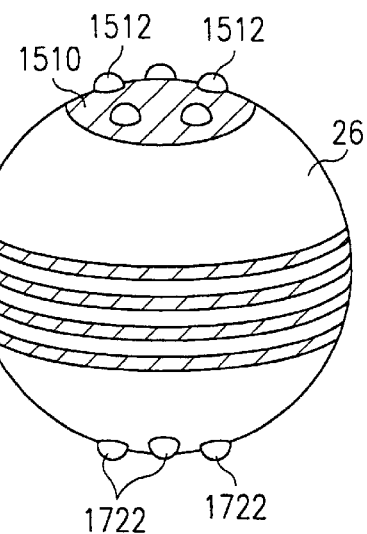
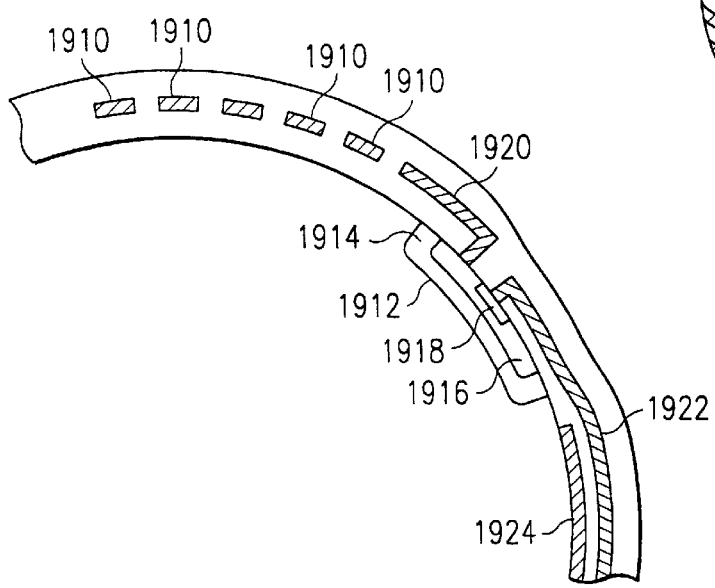
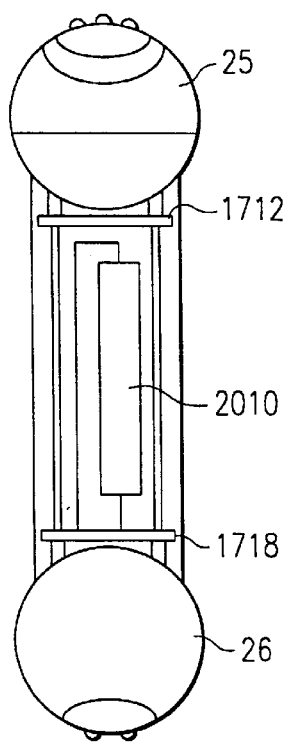
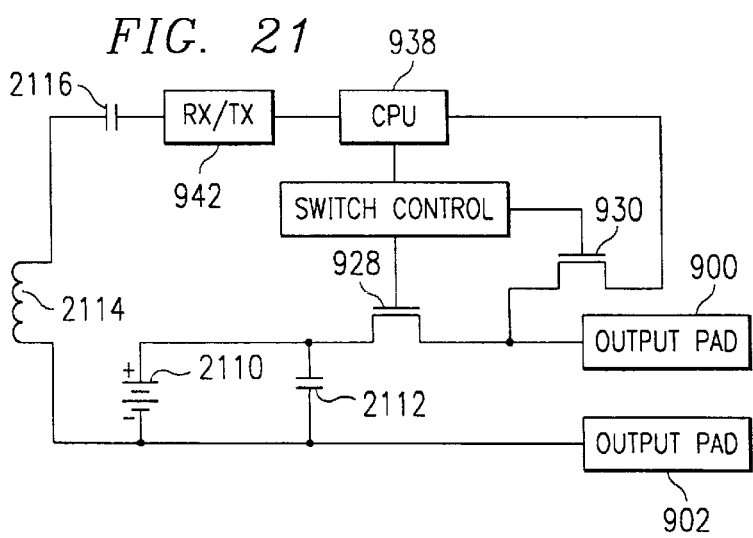

IMPLANTABLE EPICARDIAL ELECTRODE

CROSS REFERENCE TO RELATED APPLICATIONS

This application is related to the following commonly assigned patent applications: U.S. Ser. No. 60/110,103 entitled "Miniature Spherical-Shaped Semiconductor With Transducer"; U.S. Ser. No. 60/110,107 entitled Spherical-Shaped Biomedical IC" each of which were filed on Nov. 25, 1998 and each of which is incorporated herein by reference.

TECHNICAL FIELD OF THE INVENTION

The present invention relates generally to a body implantable system, and more particularly to an indwelling intramyocardial pacing and sensing electrode with wireless communication capabilities.

BACKGROUND OF THE INVENTION

Temporary bipolar epicardial atrial and ventricular pacing wires are routinely placed after major cardiac surgical procedures. Transitory changes in heart rate and rhythms following cardiac surgery are common and include sinus bradycardia, junctional rhythms, and atrioventricular heart blocks. Sinus bradycardia responds to simple atrial pacing in the range of 90–110 beats/minute. In contrast, atrioventricular blocks require both atrial and ventricular pacing to normalize atrioventricular synchrony. In fact, synchronization of atrial and ventricular contractions through the maintenance of normal sinus rhythm in the postoperative setting may account for up to 25% of the cardiac output. Tachyarrythnias are the most frequent arrythmia occurring postoperatively in some form in up to 64% of cardiac surgery patients. These fast rhythms are very detrimental and may result in atrioventricular dyssynchrony and thus, inefficient cardiac output. Overdrive atrial and atrioventricular pacing at a rate faster than the patient's spontaneous sinus rate usually suppresses paroxysmal atrial tachycardia. Atrial flutter can be interrupted through entrainment with atrial pacing at a rate slightly greater than the atrial flutter rate to recapture the atria. Following recapture, termination of the pacing is usually followed by a return to normal sinus rhythm. Rapid atrial stimulation (pacing) at rates up to 600 beats per minute for periods of less than one second may also be used in cases of atrial flutter to interrupt the flutter cycle. In some cases, atrial fibrillation, the most common postoperative supraventricular arrhythmia following cardiac surgery can also be converted using entrainment or rapid atrial pacing.

Postoperative ventricular tachyarrhythmias are potentially fatal. Differentiating ventricular tachycardia from sinus tachycardia with a bundle branch block or a supraventricular tachyarrythmia with aberrant conduction may be difficult. Direct recording from the epicardial atrial and ventricular bipolar pacing electrodes can lead to the definitive diagnosis which will direct the manner of treatment and prevent possible complications from inadvertent treatment.

Temporary atrial or atrioventricular pacing may decrease the need for inotropic support in the immediate postoperative period. Temporary pacing may be required for up to 48 hours for treatment of postoperative bradyarrhythmias. Routinely, most epicardial leads are left in place for up to 96 to 120 hours. Indwelling epicardial leads are potential sources for infection and may result in the development of mediastinitis. Mediastinitis can occur in up to 2% of postoperative cardiac surgery patients. Wound exploration, debridement, and surgical drainage are often required to treat this serious postoperative complication. At the time of removal, these epicardial leads, which are sewn into the myocardium, are pulled out with manual traction potentially resulting in further patient morbidity.

The current invention attempts to eliminate these problems of infection and lead removal by placing an implantable small pacing electrode within the myocardium that does not require removal and is operated via radio frequency.

SUMMARY OF THE INVENTION

The present invention disclosed and claimed herein comprises an implantable medical device for implanting in tissue. An anode device is provided for conductively interfacing with the tissue as well as a cathode device for conductively interfacing with the tissue. A support structure supports the anode and cathode a predetermined distance apart. A processing system is disposed between the anode and the cathode for interfacing with the anode and the cathode devices, wherein the anode and the cathode devices allow the processing system to interface with the tissue to perform predetermined functions in association therewith.

In another aspect of the invention, the processing system is operable to sense a voltage between the anode and the cathode as the predetermined functions. The processing system is also operable to generate a voltage across the anode and the cathode as the predetermined functions. The voltage is generated for a predetermined duration of time and at predetermined intervals.

In a further aspect of the invention, the processing system further includes a communication device with a receiver for communicating with a remote system external to the tissue for receiving information therefrom. The communication system includes a transmitter and is operable to transmit data from the processing system to the remote system. The processing system has associated therewith a power supply system, the power supply system having associated therewith a storage capacitor. The communication system is operable to receive an external signal for inductively coupling power across the tissue to the power supply system for storage of energy in the capacitor, the processing system powered by the power supply system and the energy stored in the power supply capacitor.

In a yet further aspect of the present the processing system includes a memory for containing a predetermined ID therein unique to the medical device and the transmitter is operable to transmit said ID to the remote system.

BRIEF DESCRIPTION OF THE DRAWINGS

For a more complete understanding of the present invention and the advantages thereof, reference is now made to the following description taken in conjunction with the accompanying Drawings in which:

FIG. 15 illustrates a side view of the implantable epicardial electrode;

FIG. 16 illustrates an alternate embodiment of the embodiment of FIG. 15;

FIG. 16a illustrates a top view of the embodiment of FIG. 16;

FIG. 17 illustrates a cross-sectional side view of the embodiment of FIG. 15 illustrating the interconnection of the two semiconductor spheres;

FIG. 18 illustrates a perspective view of one of the semiconductor spheres having the antenna leads disposed thereon;

FIG. 19 illustrates a cross-sectional diagram of the portion of the surface of the spherical IC of FIG. 18;

FIG. 20 illustrates a cross-sectional side view of the epicardial lead for an alternate embodiment illustrating the use of an additional capacitor and/or battery; and FIG. 21 illustrates a schematic block diagram of the circuitry utilizing a battery as the primary power source.

DETAILED DESCRIPTION OF THE INVENTION

A spherical-shaped integrated circuit (IC) has been disclosed by applicant in U.S. patent application Ser. No. 08/858,004, entitled SPHERICAL SHAPED SEMICONDUCTOR INTEGRATED CIRCUIT, filed May 16, 1997, claiming benefit of U.S. Provisional Application No. 604/032,340, filed Dec. 4, 1996, which is incorporated herein by reference.

The following specific embodiments are illustrative of the use of the implantable epicardial electrode but are not intended to be limiting in the potential uses of such a device. For the purpose of the disclosed embodiment, an epicardial electrode as described herein in its broadest sense, includes a stimulating electrode, a sensing electrode, or any combination thereof which may be usefully introduced into the body.

The disclosed embodiment provides an implantable intro-myocardial electrode to be sewn into the atria and ventricular myocardium at the time of surgery. The electrode is bipolar and able to function both as a sensing and pacing electrode.

Figure 1:
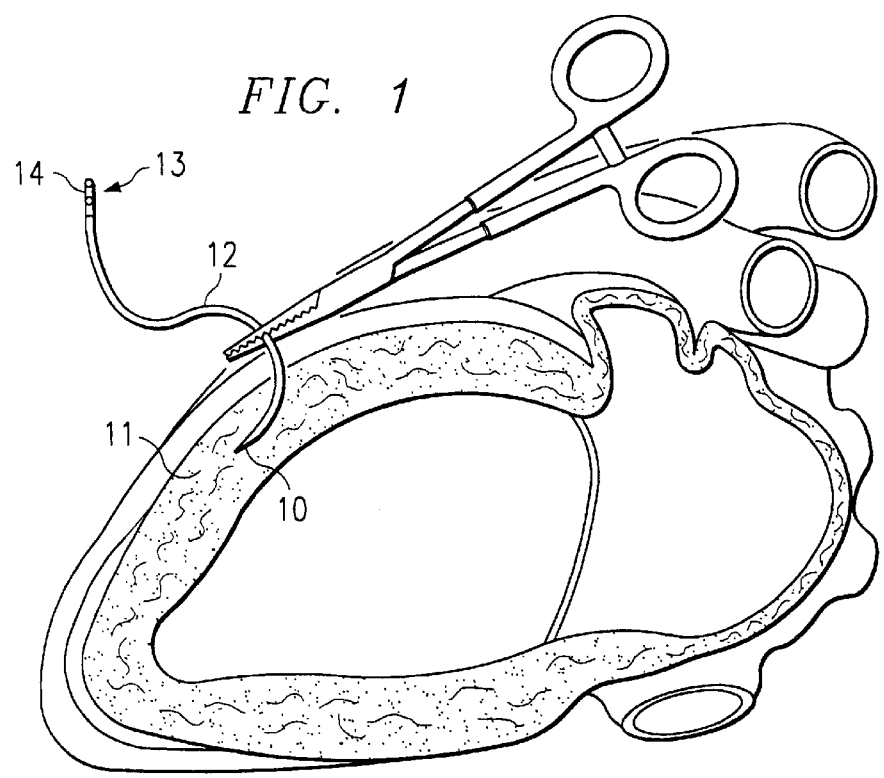
FIG. 1 illustrates the surgical insertion of the electrode system into the myocardium during cardiac surgery.

FIG. 1 illustrates a cross-sectional view of the heart, as a suture needle 10 is placed into the ventricular myocardium 11. Attached to the end of a suture thread 12 is an implantable epicardial electrode 13. The epicardial electrode 13 is attached to the suture thread 12 by smaller tensile threads that are attached to a lead body 14. The suture needle 10 is passed in and out of the myocardium 11 in a sweeping arch midway through the myocardium 11. The thread 12 is drawn until the electrode 13 is pulled totally within the myocardium 11. The suture needle 10 is passed one additional time at a 90-degree angle to the electrode and slightly deeper (not shown). The suture thread 12 is then drawn taut and the suture thread 12 is then tied at the epicardial surface. This additional stitch at 90 degrees to the electrode 13 and slightly deeper in location ensures that the electrode 13 is maintained in place within the myocardium 11. An additional epicardial electrode is placed within the atrial myocardium in a similar manner.

Figure 2A:
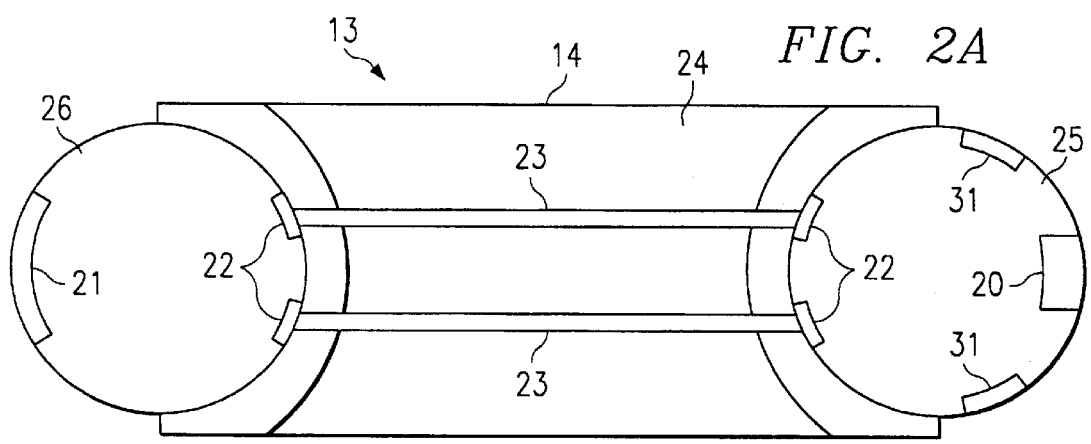
FIG. 2a is a plan view of the epicardial lead.
Figure 2B:
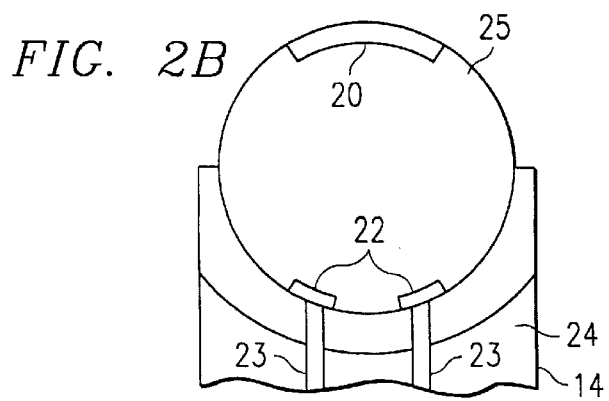
FIG. 2b is an enlarged view of the epicardial lead.

Referring now to FIGS. 2a and 2b, there is illustrated a sectional view of the electrode 13. Attached to the lead body 14 is an anode semiconductor ball 25 with an impulse generator 20 for cardiac pacing purposes and in addition functions as the anode of the electrode assembly. At the other end of the device 13 is a second electrical sensor functioning as the cathode 21 of the electrode assembly 13. This is fabricated on a cathode semiconductor ball 26. The distance between the impulse generator 20 (anode) and the cathode portion 21 of the electrode 13 is approximately 0.5 cm. This distance has been found to be particularly effective in temporary pacing electrodes. Positioned on opposite poles of the impulse generator ball are situated two conduction plates 22. These conduction plates are in contact with two or more thin metal wires 23, which communicate with the cathode located on the second semiconductor ball. The cathode electrode ball is constructed in a similar fashion to the impulse generator ball with two conducting plates 22 located at the opposite pole from the cathode. Thus, direct communication takes place through the wires between the two balls allowing feedback signals to be received by the impulse generator ball. Separating the two balls and located around and in between the two connecting wires is a non-conducting substance 24, preferably silicone in this embodiment, serving as an insulator and also as a support structure.

Figure 3:
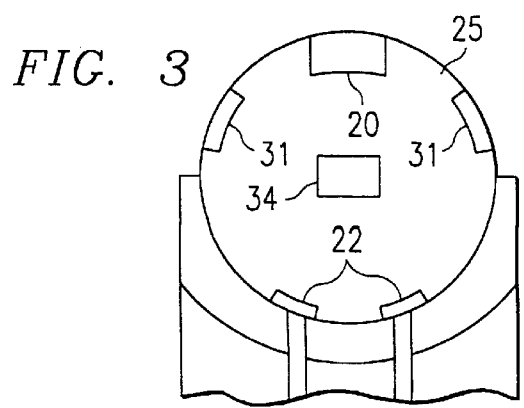
FIG. 3 is an enlarged view of an alternative embodiment of the impulse generator pacing end of the epicardial lead.

Referring now to FIG. 3, there is illustrated another embodiment of the impulse generator end of the electrode 13 containing two additional flanking electrodes 31 for detection of electrocardiographic activity within the myocardium 11. These flanking electrodes 31 may also have indirect input to the impulse generator 20 through a ball logic unit 34 located upon the ball electrode and described in more detail in FIG. 4 hereinbelow.

Figure 4:
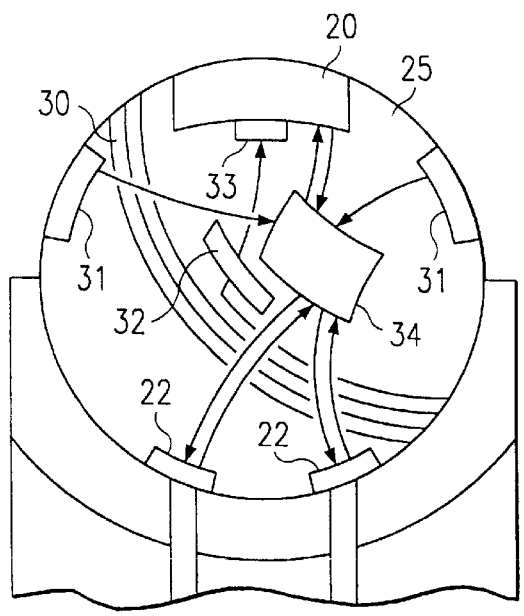
FIG. 4 is a more detailed view of the impulse generator.

Referring now to FIG. 4, a more detailed view of the anode semiconductor ball 25 of the electrode 13 is illustrated. The impulse generator 20 receives power from antenna coils 30 wrapped circumferentially around the anode ball 25. The power signal is derived from radio frequency generated outside the body from a central processing unit (not shown) by inductive coupling. The signal moves through a radio frequency rectifier and smoother 32 before being sent to a DC power storage unit 33 where it can be periodically sent to the impulse generator 20 to create a DC electrical excitation signal for cardiac pacing. The impulse generator 20 receives communication from a ball logic unit 34. The ball logic unit 34 also receives information from the flanking electrodes 31 and cathode semiconductor ball through the conduction plates 22.

In another embodiment, the ball logic unit 34 can serve as a processor of electrocardiographic signals detected by the flanking electrodes 31. In this manner, the epicardial electrode can function as a direct atrial and ventricular detection electrode for monitoring difficult to interpret tachyarrhythmias. The analog signal detected by the flanking electrodes is converted to a digital signal; directed through a radio frequency modulator; filtered; amplified; routed through the radio frequency coils for transmission to a central processing unit located outside the body for analysis or storage and displayed in more detail in FIGS. 6–8 hereinbelow.

Figure 5:
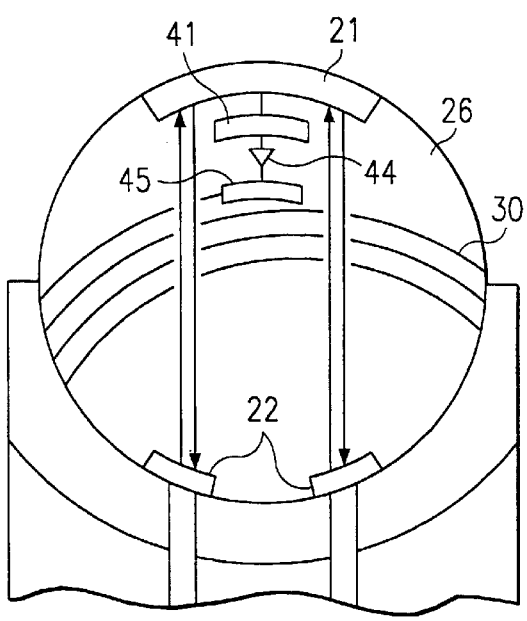
FIG. 5 is an enlarged view of the cathode end of the lead.

Referring now to FIG. 5, there is illustrated a further enlargement of the cathode semiconductor ball 26 of the epicardial electrode 13. In another embodiment, the cathode portion 21 may function as a direct myocardial electrode, either in the atrium or ventricle. The electrical potential detected by the electrode depicted in this diagram as reference numeral 21 is first sent to an analog-to-digital converter 41 where it is further modulated, filtered, amplified by an amplifier 44, and finally transmitted through an oscillator and modulator 45 to derive a signal suitable for radio frequency transmission via antenna/coils 30 to an external central processing unit (not shown) for analysis or storage and described in more detail in FIGS. 6–8 hereinbelow. In addition, electrical signals are both transmitted and received by the cathode 21 through the conducting plates 22 located on the opposite side of the cathode semiconductor ball 26. This provides the connection between the impulse generator 20 (anode) and the cathode 21 of the epicardial electrode assembly 13.

Figure 6:
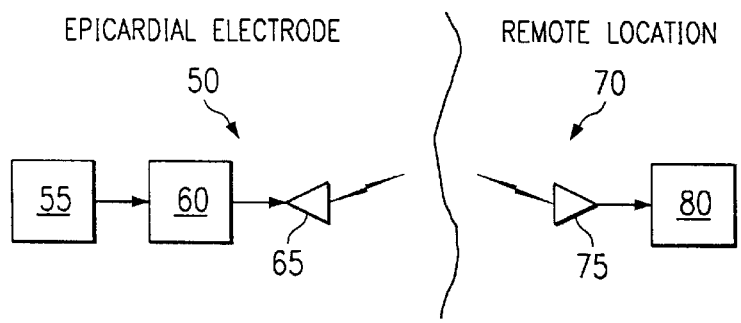
FIG. 6 displays a block diagram of the epicardial electrode.

Referring now to FIG. 6, there is illustrated a block diagram of the processing system for processing of signals taken from the electrode 13. As shown in FIG. 6, an epicardial electrode 50 of this invention for monitoring electrical activity of the heart and capability to transmit to a remote location 70 comprises (a) a detector 55 for detecting the electrical potential generated by the electrode and generating a signal indicative of the detected electrical heart activity; (b) a processor 60 for processing the generated electrical signal for transmission from the epicardial electrode 50 using a wireless communication link; (c) a transmitter 65 for wirelessly transmitting the generated electrical signal to a remote location; (d) a receiver 75 at the remote location for receiving the transmitted electrical signal; and (e) a processor 80 at the remote location for processing the received electrical signal for the purpose of extracting from the electrical signal information about the detected electrical activity.

Figure 7:
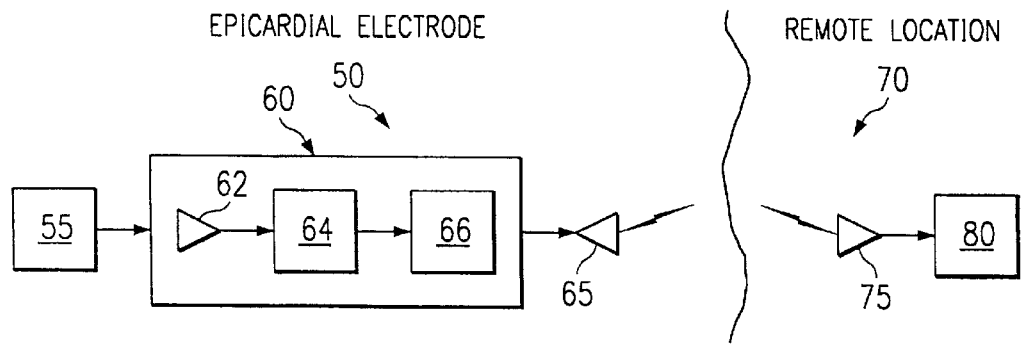
FIG. 7 displays a more detailed block diagram of the epicardial electrode.

Referring now to FIG. 7, there is illustrated a more detailed block diagram of the embodiment of FIG. 6. The processor 60 comprises a comparator amplifier 62, a noise filter 64, and an analog-to-digital converter 66. The comparator amplifier 62 is operable to receive the electrical signals detected by the electrode 13 and generate an analog signal indicative of the electrical potentials measured across each of the electrodes. The noise filter 64 removes noise signals from the generated analog signal and the analog-to-digital convertor 66 converts the analog signal into a digital signal representation of the detected electrical heart activity for transmission to the remote location using the wireless communication link.

Preferably, the transmitter 65 for transmitting the digitized electrical signal is a telemetry transmitter device operating at radio frequencies. Any wireless transmission technique may be used. In addition, the receiver 75 at the remote location for receiving the digitized transmitted electrical signal is likewise a telemetry receiver device operating at radio frequencies or some other wireless receiver that is compatible with the transmitted signal.

FIGS. 6 and 7 also illustrate the processor 80 at the remote location for processing the received digitized electrical signal. This processor 80 is operable to interpret the received digitized electrical signal.

Figure 8:
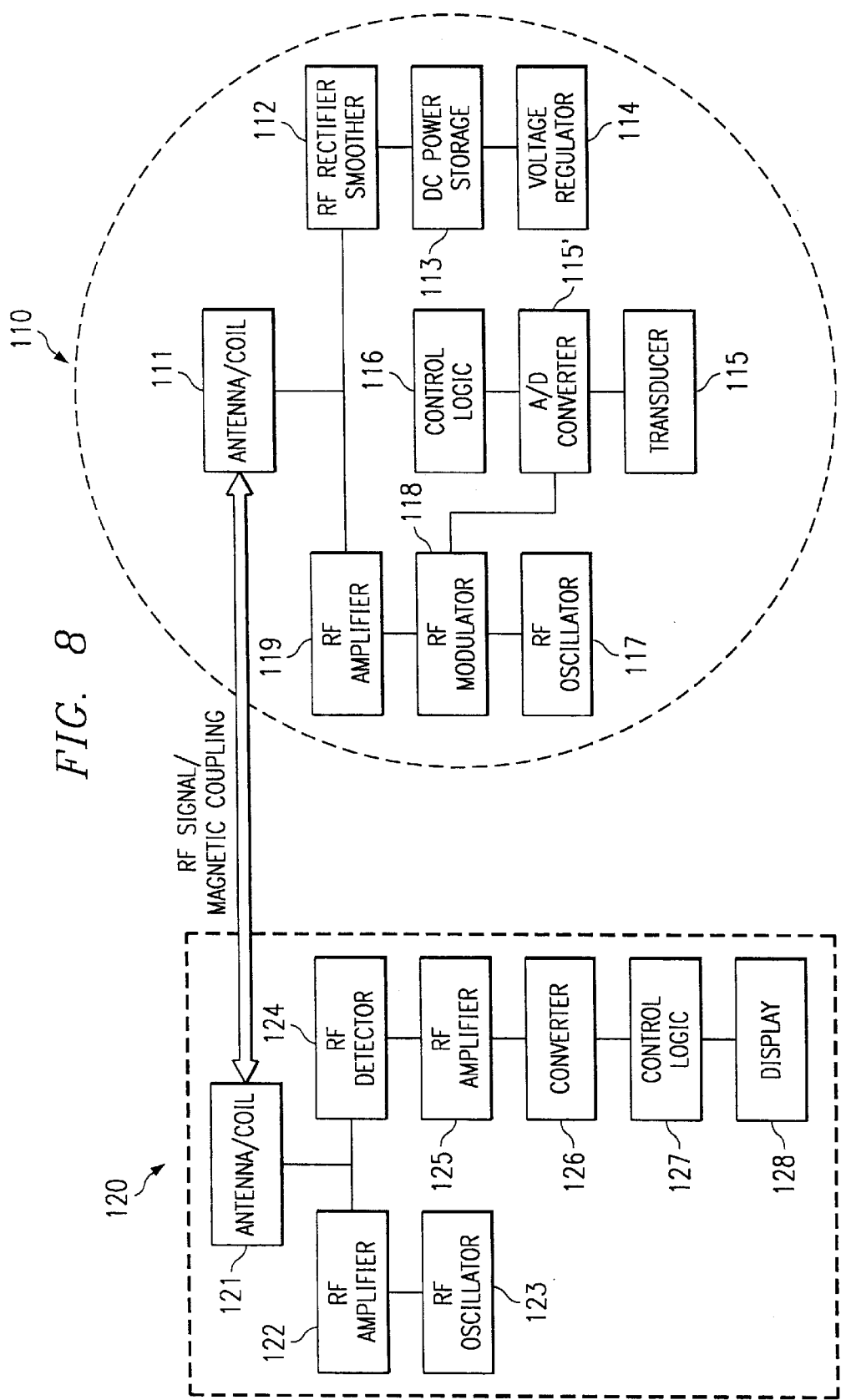
FIG. 8 is a block diagram of a ball with an integral transducer in combination with a radio frequency communication system in accordance with the present invention.

Referring now to FIG. 8, the basic circuit functions of the epicardial electrode 13 are illustrated. Semiconductor ball 110 includes an antenna/coil 111, which serves the dual purpose of receiving signal energy from a central processing unit 120 and transmitting signal energy thereto. The signal energy may be received by the antenna/coil 111 by inductive coupling if the central processing unit 120 is sufficiently close to the ball 110. Alternatively, electromagnetic waves can be used to transmit power from the central processing unit 120 to the ball 110, whereby the magnetic field component of the electromagnetic wave induces a current in the coil 111 in accordance with known techniques. The power signal received by the antenna/coil 111 is rectified and smoothed by a radio frequency rectifier smoother circuit 112. The output of the circuit 112 is connected to a DC power storage device 113, such as a capacitor. Such capacitor might also perform a waveform smoothing function. A voltage regulator 114 is used to make the DC voltage stable regardless of the distance between the central processing unit 120 and the ball 110.

The ball 110 includes the impulse generator, anode and cathode portions of the electrode, and flanking electrodes and are co-labeled in this diagram as transducer 115 and may function either as sensors or actuators. In this particular example, the impulse generator functions as an actuator and the anode, cathode, and flanking sensors function as electrical sensors. Such semiconductor electrical sensors and impulse generators are known in the art and can be adapted to fabrication on a spherical semiconductor substrate as previously described in commonly-assigned U.S. Patent Application entitled "Spherically-Shaped Biomedical IC" which is hereby incorporated by reference.

An analog-to-digital converter 115' is used to convert the electrical signal sensed by the electrodes 115 to a signal that can be transmitted out to the central processing unit 120. The converter 115' can be part of the transducer 115, such as a variable capacitor for generating a signal depending upon the variations in capacitance. Control logic 116, which can be part of an on board processor that controls not only the converter 115' but also circuitry on the ball 110, is provided in accordance with known techniques.

A radio frequency oscillator 117 generates a radio-frequency carrier signal at a predetermined frequency in the radio frequency band. A radio frequency modulator 118 modulates the output of the converter 115' onto the carrier frequency signal. The resulting modulated signal is amplified by a radio frequency amplifier 119, and then transmitted to the outside through the antenna/coil 111. Further details of the preferred coil are described in the aforementioned commonly assigned U.S. Patent Application entitled "Miniature Spherical-Shaped Semiconductor With Transducer."

An external central processing unit 120 includes an antenna/coil 121 that serves the dual purpose of generating the electromagnetic wave for transmitting power to the ball 110, and receiving the radio frequency data signal transmitted by the ball 110. It is preferred that the frequency of the electromagnetic wave that is output by the antenna/coil 121 is different from the carrier frequency generated by the radio frequency oscillator 117. A radio frequency amplifier 122 is used to couple the electromagnetic wave for power transmission to the antenna/coil 121. Radio frequency oscillator 123 determines the frequency of the electromagnetic wave that is emitted by the central processing unit 120. The data received by the antenna/coil 121 is detected by a radio frequency detector 124 and then amplified by a radio frequency amplifier 125. Preferably, the converter 126 converts the signal from the radio frequency amplifier 125 to a digital signal, which in turn is input to control logic 127. The control logic 127 may be a smaller central processing unit to interface with the main central processing unit 120. The control logic 127 extracts the data from the signal received by the central processing unit 120 from the ball 110 and displays that information on a suitable display 128, such as a CRT screen.

The technique for transmitting data from the ball 110 to the main central processing unit 120 using the carrier frequency generated by the radio frequency oscillator 117 can be in the form using any suitable protocol. The modulation can be AM, FM, PM, or any other suitable modulation technique.

Those skilled in the art will recognize that the described epicardial pacing electrode can be employed to both stimulate the myocardium electrically as well as to detect myocardial electrical activity. Control of the epicardial electrode is via wireless remote frequency eliminating problems with infections which gain access to the mediastinum via the trans-thoracic epicardial wires currently in use. Moreover, poor connection with the current wires to the monitor box can result in epicardial lead sensing and pacing malfunction.

Figure 9:
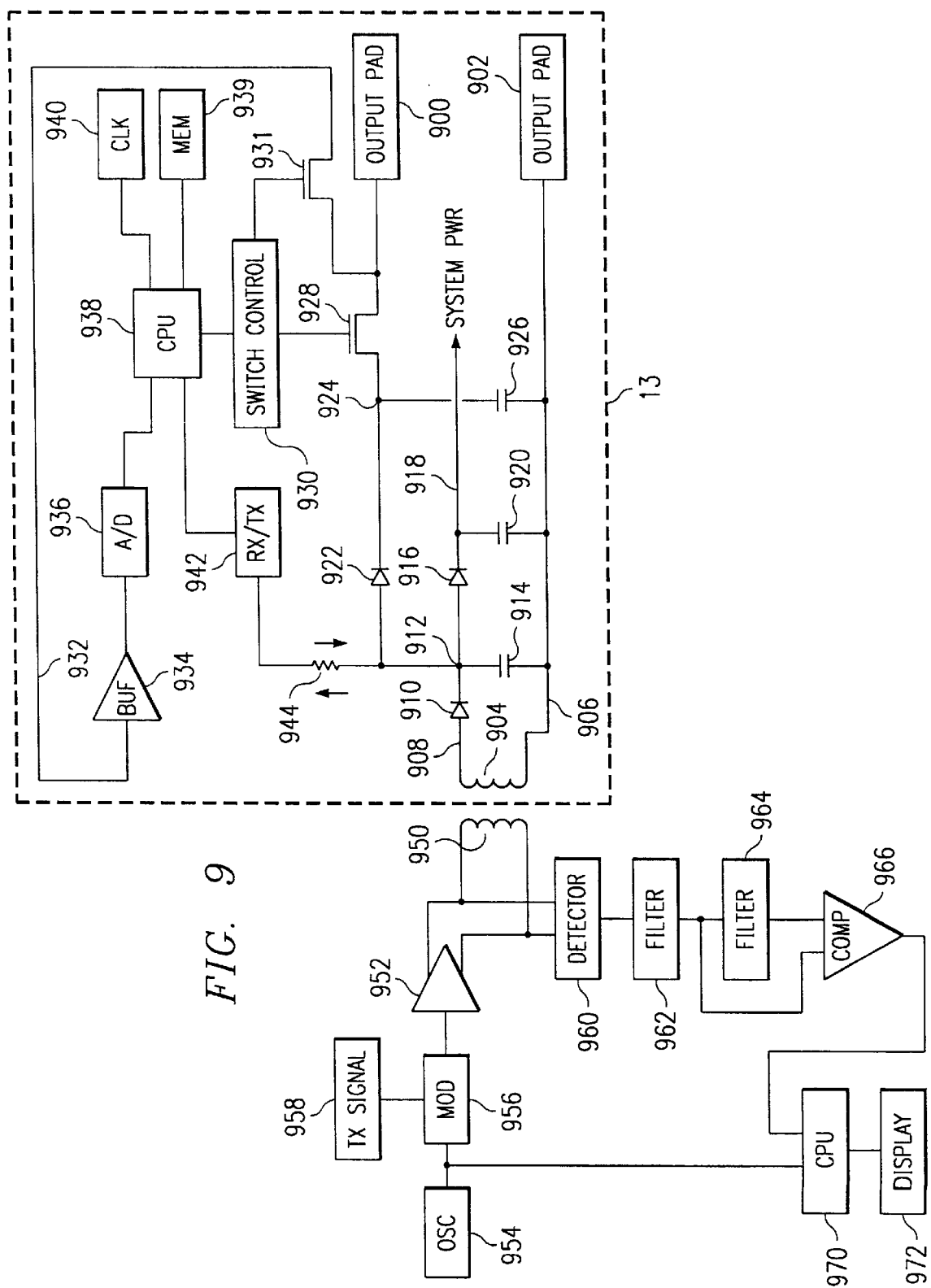
FIG. 9 illustrates a schematic block diagram of the receiver/transmitter and a detection/power system.

Referring now to FIG. 9, there is illustrated a schematic block diagram of the epicardial lead 13 and the remote system for the powering/detection operation. The epicardial lead 13, as described hereinabove, is operable to provide two output interfaces, an output pad 900 as an anode and an output pad 902 as a cathode, for interfacing with the cardiac muscle tissue. The spacing between these two pads or contacts 900 and 902 is approximately 0.5 cm. The illustrated embodiment of FIG. 9 is that associated with a "passive" system, which term refers to the fact that there is no battery associated therewith. In order to operate the system, there is provided an inductive coupling element 904 in the form of an inductor, which is operable to pick up an alternating wave or impulse via inductive coupling and extract the energy therein for storage in the inductive element 904. This will create a voltage across the inductive element 904 between a terminal 906 and a terminal 908. A diode 910 is connected between the node 908 and a node 912, with the anode of diode 910 connected to node 908 and the cathode of diode 910 connected to a node 912. Typically, the diode 910 will be fabricated as a Schottky diode, but can be a simple P/N semiconductor diode. For the purposes of this embodiment, the P/N diode will be described, although it should be understood that a Schottky diode could easily be fabricated to replace this diode. The reason for utilizing a Schottky diode is that the Schottky diode has a lower voltage drop in the forward conducting direction.

The diode 910 is operable to rectify the voltage across the inductive element 904 onto the node 912, which has a capacitor 914 disposed between node 912 and node 906. Node 912 is also connected through a diode 916 having the anode thereof connected to node 912 and the cathode thereof connected to a node 918 to charge up a capacitor 920 disposed between node 918 and 906. The capacitor 920 is the power supply capacitor for providing power to the epicardial lead 13. The capacitor 914, as will be described hereinbelow, is operable to be discharged during operation of the system and, therefore, a separate capacitor, the capacitor 920, is required for storing power to power the system.

The node 912 is connected to the anode of a diode 922, the cathode thereof connected to a node 924. Node 924 is connected to one side of a main capacitor 926, the other side thereof connected to node 906. The capacitor 926, as will be described hereinbelow, is operable to provide the primary discharge energy to the myocardium. This node 924 is connected to one side of the gate/source path of a transistor 928, the other side thereof connected to the output pad 900. The gate of transistor 920 is connected to the output of a switch control circuit 930. Transistor 920 is operable to be turned on for a short period of time to connect to the top plate of capacitor 926 to the output pad 900 and subsequently, to conduct current to the myocardium.

In addition to transmitting energy out on pad 900, there is also provided a second sense transistor 931 which has one side of the gate/source path thereof connected to the output pad 900 and the other side thereof connected to a node 932. The gate of transistor 931 is connected to the output of the switch control 930. Node 932 is connected to the input of a buffer 934 to generate an analog signal output thereof which is then converted with an analog-to-digital converter 936 to a digital value for input to a central processing unit (CPU) 938. The CPU 938 is operable to receive and process this digital input voltage. A clock circuit 940 is provided for providing timing to the system. A memory 939 is provided in communication with the CPU 938 to allow the CPU 938 to store data therein for later transmittal back to the remote location or for even storing received instructions. This memory 939 can be volatile or it can be non-volatile, such as a ROM. For the volatile configuration, of course, this will lose all information when the power is removed.

The CPU 938 is operable to provide control signals to the switch control 930 for turning on the transistor 928 or the transistor 931 at the appropriate time. Typically, the transistor 928 is controlled to turn on for a period of approximately 0.5 microseconds 60–80 times per minute. Once transistor 928 is turned off, then transistor 931 can be turned on. Alternatively, transistor 931 could be a pass-through circuit such that the CPU 938 can always monitor the voltage on the output pad 900. However, it is desirable with the transistor 931 and the sensing operation to sense depolarization in the myocardium after an output voltage has been provided thereto for a short duration of time.

In order to communicate with the CPU 938 for transferring data thereto and for allowing the CPU 938 to transfer data therefrom, a receive/transmit circuit 942 is provided for interfacing to node 912 to a resistive element 944. This allows radio frequency (RF) energy to be transmitted to node 912. It is important to note that the semiconductor junction across diode 910 is a capacitive junction. Therefore, this will allow coupling from node 912 to node 904. Although not illustrated, this could actually be a tuned circuit, by selecting the value of the capacitance inherent in the design of the diode 910. In any event, this allows an RF connection to be provided across diode 910 while allowing sufficient energy to be input across conductive element 904 to provide a voltage thereacross for rectification by the diode 910 and capacitor 914. Typically, the frequency of this connection will be in the MHz range, depending upon the design. However, many designs could be utilized. Some of these are illustrated in U.S. Pat. Nos. 4,333,072 and 3,944,982, which are incorporated herein by reference. With these types of systems, power can continually be provided to the node 912 and subsequently to capacitors 920 and 926 to allow power to be constantly applied to the epicardial lead. The diode 922 may not be required in order to provide the sufficient charge to capacitor 926, but some type of isolation is required between the capacitor 926 and the capacitor 920. Additionally, it may be that some voltage regulation is required in order to provide a shaped pulse on the output pad 900. This could be provided by the switch control 930.

The remote system which is disposed outside of the body and proximate to the epicardial lead 13 includes an inductive element 950 which is operable to be disposed in an area proximate to the skin exterior to the body in the proximity of the epicardial lead 13. The inductive element 950 is driven by a driving circuit 952 which provides a differential output that is driven by an oscillator 954. This will be at a predetermined frequency and power level necessary to couple energy from inductive element 950 to inductive element 904. Since this is an external system, the power of the oscillator can be set to a level to account for any losses through the body tissues. To allow information to be transmitted, a modulation circuit 956 is provided which is modulated by a transmitter signal in a block 958 that allows information to be modulated onto the oscillator signal 954, which oscillator 954 is essentially a "carrier" signal. However, it should be understood that the information that is transmitted to the epicardial lead 13 could merely be date information whereas the CPU 938 could operate independent of any transmitted information to provide the correct timing for the output pulses and the correct wave shape therefor. Alternatively, the entire control of the system could be provided by the transmit signal 950 and the information carried thereon, since power must be delivered to the illustrated embodiment due to the lack of any independent power in the epicardial lead 13.

When the information is received from the epicardial lead 13, it is superimposed upon the oscillator signal driving the inductive element 950. This is extracted therefrom via a detector 960 which has the output thereof input to a first low pass filter 962 and then to a second low pass filter 964. The output of low pass filters 962 and 964 are compared with a comparator 966 to provide the data. The filter 962 will provide an average voltage output, whereas the filter 964 will provide the actual digital voltage output. The output of the comparator 966 is then input to a CPU 970 which also is powered by the oscillator 954 to process the data received therefrom. This can be input to a display 972.

Figure 10A:
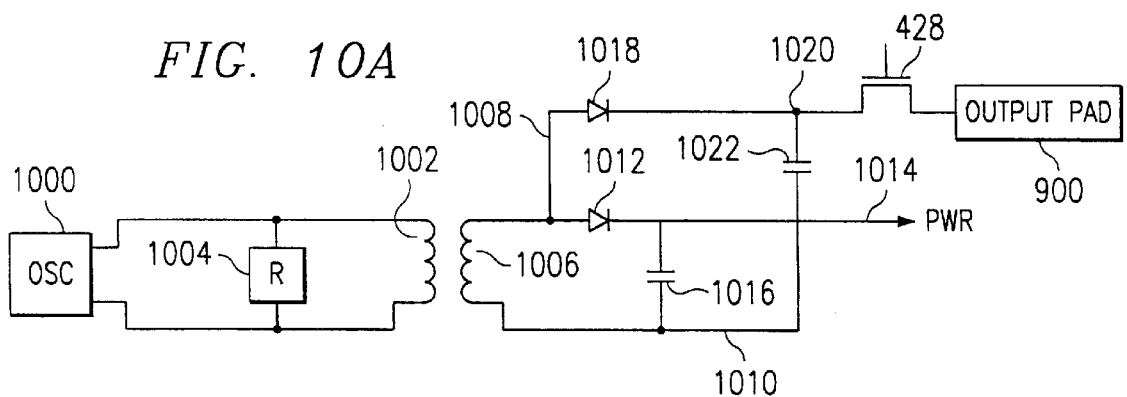
FIGS. 10a–10c illustrate alternative embodiments for the receiver/transmitter and the storage capacitors associated therewith.
Figure 10B:
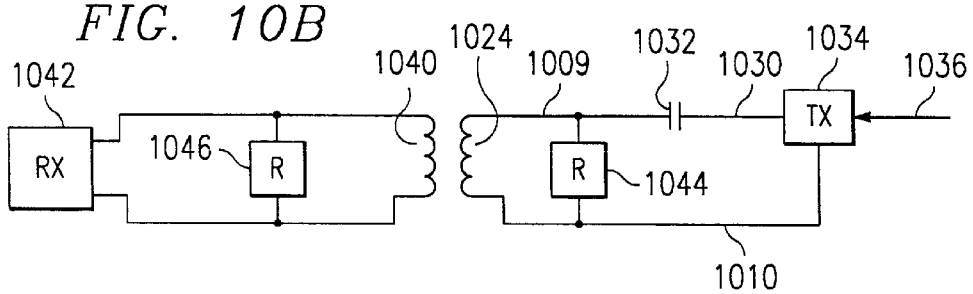
Figure 10C:
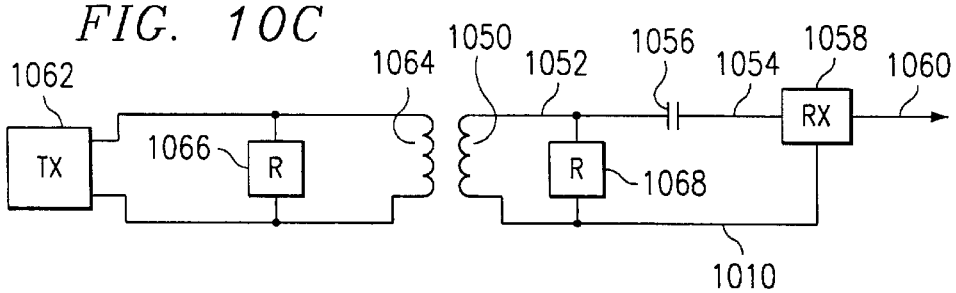

Referring now to FIGS. 10a–10c, there are illustrated alternate embodiments for the transmit/receive operation. In FIG. 10a, there is provided an oscillator 1000 which drives an external inductive element 1002. Typically, there is some type of load 1004 disposed across the inductive element 1002. This is the primary power that is provided to the system. A separate inductive element 1006 is provided on the epicardial lead 13, for being inductively coupled to the inductive element 1002. Thereafter, a voltage is generated across the inductive element 1006, the inductive element 1006 being connected between a node 1008 and 1010. A diode 1012 is connected between node 1008 and a power node 1014, a power supply capacitor 1016 disposed across node 1014 and node 1010. This allows the voltage on node 1006 to be rectified with diode 1016. Similarly, a diode 1018 is connected between node 1008 and a node 1020 which is connected to one side of a main capacitor 1022. The other side of capacitor 1022 is connected to node 1010. This capacitor 1022 is similar to the main capacitor 926 in FIG. 9. The switch transistor 928 is provided for connecting the node 1020 to the output pad 900.

The receive operation in this embodiment utilizes a separate inductive element or antenna 1024 in the epicardial lead 13, which is operable to be connected between nodes 1009 and 1010. Node 1009 is capacitively coupled to a transmit node 1030 with a capacitor 1032, the capacitor 1032 being a coupling capacitor. A transmitter 1034 is provided for transmitting received data from a line 1036 to the node 1030 which is then coupled to the node 1009 to impress the RF signal across the inductive element 1024.

A corresponding inductive element 1040 is disposed on the external remote controller, which inductive element 1040 is operable to be disposed proximate to the inductive element 1024, but external to the human body. The inductive element 1040 is basically a "pick-up" element which is operable to receive information and function as an antenna and provide the received signal to a receiver 1042. The structure of FIG. 10b is a separate structure, such that node 1009 is isolated from node 1008, the power receiving node. However, it should be understood that any harmonics of the oscillator 1000 would, of course, leak over into the inductive element 1006. This can be tuned out with the use of some type of tuning element 1044 on the epicardial lead 13 disposed across inductive element 1024 and also a tuning element 1046 disposed across the inductive element 1040, i.e., the antenna.

Referring now to FIG. 10c, there is illustrated a simplified schematic diagram of the receive portion. The epicardial lead 13 has associated therewith a separate receive antenna or inductive element 1050 disposed between node 1010 and a node 1052. Node 1052 is capacitively coupled to a receive node 1054 with a coupling capacitor 1056. A receiver 1058 is provide for receiving the information transmitted thereto and providing on the output thereof data on a data line 1060. The receiver 1058 is operable to receive the RF signal, demodulate the data therefrom, and provide digital data on the output 1060. External to the human body and the epicardial lead 13 is a transmitter 1062 which is operable to impress a signal across an external inductive element 1064. The inductive element 1064 basically provides the RF energy and is essentially tuned with a tuning element 1066. A corresponding tuning element 1068 is provided on the epicardial lead 13 and disposed across inductive element 1050, the inductive element 1050 acting as an antenna, as well as the inductive element 1064.

Figure 11:
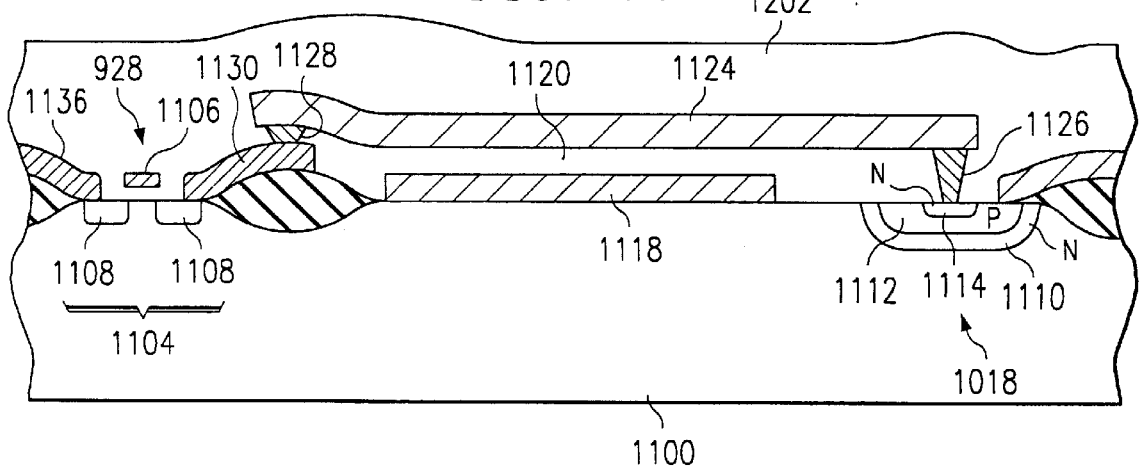
FIG. 11 illustrates a cross-sectional diagram of the primary storage capacitor.

Referring now to FIG. 11, there is illustrated a cross-sectional view of the semiconductor device in the form of the spherical IC which has been "planarized" to remove the curvature thereof for discussion purposes. The semiconductor substrate is noted as a reference terminal 1100 and has disposed thereon various integrated circuits. In general, the circuit illustrated in FIG. 11 is the main capacitor 1022, the diode 1018 and the transistor 928. During fabrication, multiple layers of conductive material are disposed on the substrate separated by insulating oxide layers. These can be polycrystalline silicon layers or they can be metal layers.

In the disclosed embodiment of FIG. 11, the first step in the process is to form active areas. A first active area is defined for forming the transistor 928. This transistor 928 is formed by first defining an active area 104 and then depositing a thin layer of gate oxide thereover by conventional techniques. A gate electrode 1106 is then formed by depositing a layer of polycrystalline silicon on the substrate, patterning and etching that substrate to define the gate electrode separated from the surface of the silicon by a gate oxide layer. The edges of the gate electrode 1106 are then utilized to form source/drain implants 1108 on either side thereof. Disposed therebetween is a channel region. Similarly, during the processing in a P-type substrate, wherein the source/drain implants 1108 are N-type substrate material, an type implant region 1110 is formed followed by the formation of a P-implant region 1112 therein with an N-type contact region 1114 disposed within the region 1112. The region 1112 and the region 1114 essentially form a PN diode, the diode 1018. Once the active devices have been fabricated, another layer of polycrystalline silicon is disposed onto the substrate and etched to form various layers. One structure is the a lower capacitor plate 1118, over which is deposited a layer of oxide 1120. This is the capacitor oxide. This layer of oxide 1120 can be deposited to as thin a layer as possible without resulting in a significant amount of defects which will basically destroy the quality of the resulting capacitor. After this structure 1118 is formed, typically from a second layer of polycrystalline silicon or even from the first layer of polycrystalline silicon that was utilized to form the gate electrode 1106, a subsequent process step will form a metal layer 1124 thereover. The effective area of the capacitor and the thickness of the dielectric and the type of material utilized as the dielectric will define the capacitor value. Typically, a thickness of between 300Å to 500 Å can be deposited for the gate oxide. Various techniques can provide a silicon dioxide deposition on the order of 100 Å. However, the thinner the capacitor dielectric layer, the more susceptible a large area capacitor is to processing problems which can result in a large number of defects in the capacitor. These are essentially small conductive "shorts" between the layer 1124 and the structure 1118. The capacitance value is directly proportional to the inverse of the thickness.

Prior to the formation of the structure 1124, vias 1126 and 1128 are formed through oxide layer which was previously deposited to expose a portion of the N-region 1114 and also a portion of a contact structure 1130 that is the conductive layer contacting the source/drain region 1108 of the transistor 928. The vias 1126 and 1128 are then filled with a conductive plug of polycrystalline silicon or metal to provide a conductive connection between one side of the upper capacitor plate formed from the structure 1124 to the diode 1018 and the transistor 1104. The other side of the transistor 928, the source/drain region 1108, is connected to an opposite side contact 1136 which will connect to the output pad 900.

With the structure of FIG. 11, there is provided a capacitor in series with a diode. Although not illustrated, the structure 1118, comprising the lower plate of the capacitor, is connected to the ground node which constitutes the output pad 902. The area of this structure 1118 must be substantially the same as that of the upper structure 1124, the effective area being that of the overlap between the two structures. As will be described hereinbelow, the plate structures comprise a very large portion of the surface of the spherical IC to provide a sufficient amount of capacitance. For the present application of a pacemaker, the capacitor must store enough energy to deliver approximately 25 micro joules of energy to the surrounding myocardium. This can be accomplished by increasing the area of the capacitor, decreasing the width of the capacitor or increasing the voltage across the capacitor (the stored energy being directly proportional to the square of the voltage).

Figure 12:
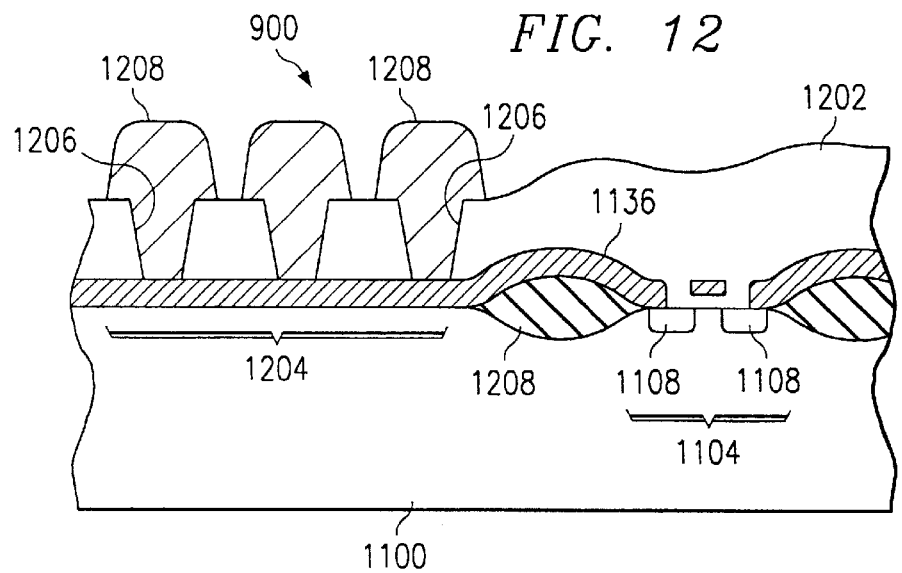
FIG. 12 illustrates a cross-sectional diagram of the conductive terminal for interfacing with the exterior of the electrode.

Referring now to FIG. 12, there is illustrated a cross-sectional view of the output pad 900. In general, the output pad 900 is required to provide a conductive interface between the transistor 928 and the myocardium muscle. This therefore requires some type of metallic interface that is non-reactive. Such an interface would require a metal such as gold, platinum and the such. In the disclosed embodiment, gold would be provided.

After the formation of the upper metal layer via a deposition technique with metal such as aluminum or even copper, a passivation layer of oxide 1202 is disposed over the substrate to basically prevent oxidation of the metal layers and protect the semiconductor circuits in general. The contact layer 1136 extends beyond the active region 1104 to an output pad region 1204 and is separated from the active region 1104 by a layer of field oxide 1208 or some type of isolation oxide. There may even be some type of channel stop implant disposed below the field oxide layer 1208. The contact 1136 extends from the source/drain implant 1108 to the region 1204. This contact 1136 is required to be fairly conductive. Typically, polycrystalline silicon is not of sufficient conductivity such that some type of polysilicide process will be required, wherein the upper surface is converted to some type of silicide such as titanium disilicide to lower the surface resistivity thereof. Alternatively, a metal layer could be provided which is connected to the contact region 1136.

Once the contact 1136 is formed and the passivation layer 1202 is disposed over the entire structure, vias 1206 are formed therein. These vias are then filled with metallic plugs 1208 by forming a layer of metal over the substrate and then etching the substrate to remove the undesired portions. The metal plugs 1208 can be formed in a desirable type of metal such as aluminum or even gold. If they were formed of gold, this would allow for soldering if they were used as contacts. However, in this context, these plugs 1208 are utilized for conductivity purposes. Therefore, an aluminum plug would be sufficient if it were covered with a thin layer of gold that would be non-reactive and would not oxidize or it could, in the disclosed embodiment, be gold. However, it should be understood that any type of non-reactive metal could be utilized as long as the surface thereof is sufficiently non-reactive and the conductance of the plug is sufficiently high to result in a low resistance path between the exterior of the spherical IC and the capacitive plate 1124. The reason for this is that the stored charge must be discharged into a resistance as low as 500 Ohms and any significant resistance disposed between the upper plate of the capacitor 1124 and the exterior need be minimized.

Figure 13:
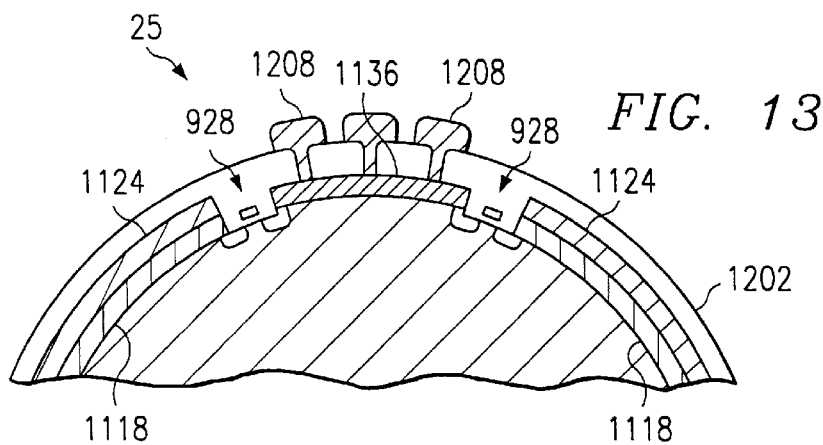
FIG. 13 illustrates a larger scale cross-sectional diagram of the conductive terminal on the spherical surface of the IC.

Referring now to FIG. 13, there is illustrated a larger cross-sectional diagram of the spherical IC illustrated with the spherical curvature of the system. It can be seen that the upper capacitor plate 1124 is disposed around substantially the entire upper hemisphere of the spherical IC 25. This is basically the anode of the epicardial lead 13. The center portion thereof is formed with the contact plate 1136 with the transistor 928 disposed therein.

Figure 14:
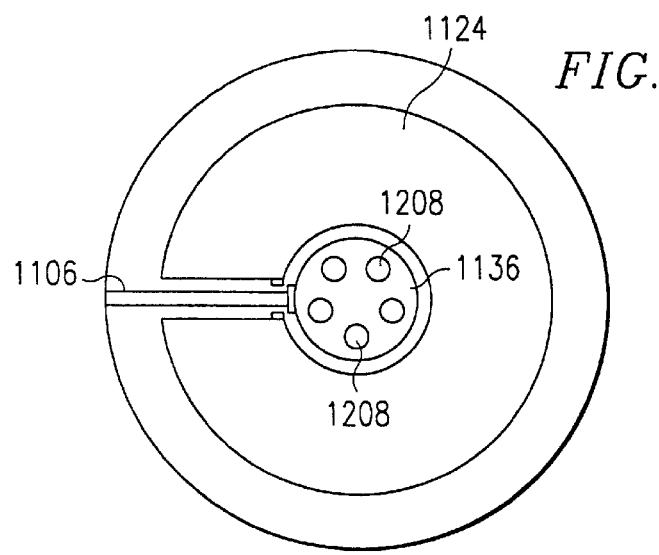
FIG. 14 illustrates a top view of the primary capacitor and conductive terminal.

Referring now to FIG. 14, there is illustrated a top view of the structure of FIG. 13. It can be seen that the transistor 928 is disposed between the contact layer 1136 and the layer 1124 (the upper plate of the capacitor) with the gate electrode 1106 connected thereto through a gap in the layer 1124. Of course, the gate electrode layer 1106 could be disposed under the layer 1124, depending upon the thickness of the separating oxide to lower the capacitance therein. Since the speeds of switching are not very high, this would probably be sufficient. Further, the entire space between the region 1136 and the plate 1124 could constitute the channel of the transistor with the source/drain implants disposed on either side and the gate electrode being disposed around the space between the two plates. This would result in a relatively long transistor and would lower the resistance thereof.

Referring now to FIG. 15, there is illustrated a side view of the epicardial lead 13. It can be seen that the anode spherical IC 25 has the capacitor plate 1136 disposed around a large portion of the area with the contact plugs 1208 disposed on the surface thereof. On the cathode spherical IC 26, there would be formed a similar contact region 1510 with contact plugs 1512 disposed thereon. This plate, of course, would not have to be anywhere near the size of the plate 1124, due to the fact that it only provides the contacts to interface with the myocardium. There would be interconnecting wires 1514 disposed between the two spherical ICs 25 and 26 with some type of resin, silicone or structural material 1516 associated therewith. Due to the fact that a relatively large amount of capacitance needs to be associated with the epicardial lead 13, the surface of the spherical IC 25 would preferably be associated with mostly capacitance, whereas the integrated circuit structure involving the receiver and other structures described hereinabove with respect to FIG. 9, will be disposed on the spherical IC 26. However, it should be understood that any of the integrated circuit structures can be disposed on either of the spherical ICs 25 or 26 or even on an additional spherical IC that could be clustered therewith. Further, it is not unreasonable that some structure could be disposed in the space between the two spherical ICs 25 and 26 which, as described hereinabove, constitutes approximately 0.5 cm of space.

Referring now to FIG. 16, there is illustrated an alternate embodiment of the epicardial lead 13 wherein a plurality of spherical ICs are clustered to replace the spherical IC 25. The upper view of this is illustrated in FIG. 16*a*. This would require a center spherical IC 1610 with a plurality of peripheral ICs 1612 disposed therearound. These would be attached to the center spherical IC 1610 with contacts 1614. The contacts 1614 and the clustering operation are described in U.S. Pat. No. 5,877,943, issued to R. Ramamurthi and assigned to the present assignee, which is incorporated herein by reference. Essentially, when utilizing the contacts 1614 for connecting in a clustered manner, gold would typically be utilized which could be bonded together.

By utilizing the clusters of spherical ICs 1612 and 1610, substantially the entire surface of the IC 1612 could be covered with a capacitor which would significantly increase the capacitance thereof. Each of the spherical ICs 1612 could have an output pad 1616 associated therewith with associated contacts similar to the contacts 1208. However, the illustrated embodiment of FIG. 16*a* only shows the center IC 1610 having the contacts. The reason for this is that a transistor would be required for each of the contacts to ensure that the associated charge would be switchably connectable to the output pad. If it were necessary to provide lower resistance, this configuration would probably be desirable. However, the resistive contact between the capacitive plate on each of the peripheral spherical ICs 1612 and the center spherical IC 1610 will provide sufficient conduction.

Referring now to FIG. 17, there is illustrated a more detailed diagrammatic view in cross-section of the embodiment of FIG. 15 illustrating the interconnection between the spherical IC 25 and the spherical IC 26. The spherical IC 25 has a plurality of interconnect balls 1710 disposed on the lower surface thereof and in connection with various circuitry and interconnects thereon. These would be soldered to some type of intermediate surface 1712 having corresponding bonding balls 1714 disposed thereon, both typically being gold. The surface 1712 would have the interconnecting lines 1514 disposed on the upper surface thereof which would interconnect to a lower structure 1718. The structure 1718 would be associated with the spherical IC 26 and have interconnection balls 1720 associated therewith with corresponding interconnection balls 1722 on the IC 26. Typically, at least one of the lines 1514 would provide a ground connection and one a positive connection. Other lines, there being anticipated to be more than two, would be provided for control information.

Referring now to FIG. 18, there is illustrated a perspective view of the spherical IC 26, wherein the inductive element is illustrated as being strips of conductive material wrapped around the exterior of the spherical IC 26. The inductive element 904 described hereinabove with respect to FIG. 9, is formed of a conductive strip wrapped many times around the spherical IC 26. The length of these wires depends upon the receive characteristics that are required. As described hereinabove with reference to FIGS. 10*a*–10*c*, there could be multiple conductive strips, each associated with a receive function, a transmit function or a power function, or they could all share one single conductive element or strip. On one end of the spherical IC 26, as described hereinabove, there is provided an anode output pad 1510 having conductive balls 1512 associated therewith of material such as gold. On the other end thereof are provided interfacing interconnect balls 1722.

Referring now to FIG. 19, there is illustrated a cross-sectional diagram of the surface of the spherical IC 26 illustrating the conductive strips forming the inductive element 902. The conductive strips are referred to by reference numeral 1910 which are spaced above the surface of the IC by a predetermined distance and separated therefrom by a layer of silicon dioxide. The passivation layer is then disposed over the upper surface of the conductive strips 1910. The conductive strips 1910 can be fabricated from polycrystalline silicon but, it would be preferable to form them from the upper metal layer to result in a lower conductivity strip. This will allow the strips 1910 to be narrower and separated from each other by a larger distance. This separation would reduce the amount of capacitance therebetween.

One end of the strips 1910 is connected to a diode structure. The diode structure is formed of an N-well implant region 1914 into which a P-well implant region 1916 is disposed, and an N-well implant region 1918 disposed within the P-well implant region 1916. This forms a PN diode where one end of the conductive strips 1910, a conductive connection 1920, is connected to the P-well 1916 implant region and a conductive layer 1922 is connected at one end to the N-well implant region 1918. This conductive layer or strip 1922 extends outward to other circuitry on the integrated circuit and can actually form the capacitor. Since it needs to go to a capacitor directly, a lower plate 1924 formed of a layer of polycrystalline silicon or metal in a double-metal process, could be provided separated therefrom by a layer of oxide.

Referring now to FIG. 20, there is illustrated a side view of an alternate embodiment utilizing additional circuitry or structure in the region between the spherical IC 25 and the spherical IC 26. As described hereinabove, the epicardial lead 13 requires two primary structures, a power supply generating structure for storing a power supply voltage such that diodes must be provided for receiving and rectifying a large amount of power and charging up a power supply capacitor, in addition to a main "surge" capacitor for providing a relatively large amount of energy to the myocardium. The space between the spherical IC 25 and the spherical IC 26 could be provided for containing either a battery or a capacitor. In the embodiment of FIG. 20 this is illustrated with a structure 2010. This is disposed between the supporting structure 1712 and 1718.

Referring now to FIG. 21, there is illustrated a schematic block diagram of the epicardial lead 13 illustrating the use of a battery. A battery 2110 is provided which is connected to a capacitor 2112. The capacitor 2112 could be identical to the capacitor 926 of FIG. 9 in that it could be formed on the surface of the spherical IC 25 or it could actually be part of the structure 2010. The battery 2110 is provided across the capacitor 2112 to provide sufficient charge therefor. Additionally, the capacitance 2112 could actually be the capacitance of the battery 2110. Additional structure could be provided for powering the CPU 938 and the other circuitry on the chip from the battery 2110. As such, there would only be required a smaller inductive element 2114 and a capacitor 2116 to allow the receive/transmit block 942 to receive/transmit information from and to the remote exterior station.

In summary, there has been provided an epicardial lead that provides the ability to be implanted within the myocardium with an anode and a cathode that are separated therefrom by a predetermined distance. Interior to the epicardial lead is circuitry for processing information and generating a stimulus to the myocardium for sensing electrical potentials in the myocardium. The epicardial lead includes a transceiver for allowing information to be received from an exterior location and transmitted thereto, the exterior location exterior to the human body and operable when proximate to the epicardial lead. Additionally, the epicardial lead can be a passive device wherein all power therefore is received from the external device.

While this invention has been described in connection with specific examples, it will be appreciated that modifications may be made without departing from the spirit and scope of the invention.

What is claimed is:

1. An implantable medical device for implanting in tissue, comprising:

first and second semiconductor devices;

an anode provided on said first semiconductor device for conductively interfacing with the tissue;

a cathode provided on said second semiconductor device for conductively interfacing with the tissue;

a support structure for supporting said first and second semiconductor devices to position said anode and cathode a predetermined distance apart; and a processing system disposed between said anode and said cathode for interfacing with said anode and said cathode, wherein said anode and said cathode allow said processing system to interface with the tissue to perform predetermined functions in association therewith.

2. The medical device of claim 1, wherein said processing system is operable to sense a voltage between said anode and said cathode as said predetermined functions.

3. The medical device of claim 1, wherein said processing system is operable to generate a voltage across said anode and said cathode as said predetermined functions.

4. The medical device of claim 3, wherein said processing system is operable to generate said voltage for a predetermined duration of time.

5. The medical device of claim 4, wherein said processing system is operable to generate said voltage for said predetermined duration of time and at predetermined intervals.

6. The medical device of claim 1, wherein said processing system further includes a communication device with a receiver for communicating with a remote system external to said tissue for receiving information therefrom.

7. The medical device of claim 6, wherein said communication system includes a transmitter and is operable to transmit data from said processing system to the remote system.

8. The medical device of claim 7, wherein said processing system has associated therewith a power supply system, said power supply system having associated therewith a storage capacitor, and wherein said communication device is operable to receive an external signal for inductively coupling power across the tissue to said power supply system for storage of energy in said storage capacitor, said processing system being powered by said power supply system and the energy stored in said storage capacitor.

9. The medical device of claim 8, wherein said processing system includes a memory for containing a predetermined ID therein unique to the medical device and said transmitter is operable to transmit said ID to the remote system.

10. The medical device of claim 8, wherein said processing system includes a memory for storing information received from the remote system, said information constituting configuration information for configuring the operation of said processing system, and wherein said processing system is configured in accordance with said stored information.

11. The medical device of claim 8 wherein said first and second semiconductor devices are each spherical in shape.

12. The medical device of claim 10, wherein said processing system includes a sensor for sensing voltage information across said anode and said cathode and storing said sensed information in said memory and wherein said transmitter is operable to transmit said information stored in said memory to the remote system.

13. The medical device of claim 8, wherein said processing system includes an impulse generator for generating a predetermined voltage across said anode and said cathode for a predetermined duration of time and powered by said power supply system.

14. The medical device of claim 13, wherein said processing system is operable to control the operation of said impulse generator in response to signals received from the remote system.

15. An implantable medical device for implanting in tissue, comprising:

an anode for conductively interfacing with the tissue;

a cathode for conductively interfacing with the tissue;

at least one of said anode or cathode with formed with an integrated circuit on a semiconductor substrate;

a support structure for supporting said anode and said cathode a predetermined distance apart;

said semiconductor substrate including a processing system;

an interconnection network for interconnecting said at least one of said anode or cathode that is formed on said semiconductor substrate to the other thereof, such that said anode and said cathode are interfaced with said processing system, and wherein said anode and said cathode allow said processing system to interface with the tissue to perform predetermined functions in association therewith; and a communication device including a receiver for receiving signals from a separate remote system external to the tissue, said processing system performing said predetermined functions in response to the signals received from the remote system.

16. The medical device of claim 15, wherein said processing system is operable to generate a voltage across said anode and said cathode as said predetermined functions.

17. The medical device of claim 16, wherein said processing system is operable to generate said voltage for a predetermined duration of time.

18. The medical device of claim 17, wherein said processing system is operable to generate said voltage for said predetermined duration of time and at predetermined intervals.

19. The medical device of claim 15, and further including a power supply system, said power supply system having associated therewith a storage capacitor, and wherein said communication device is operable to receive an external signal from the remote system for inductively coupling power across the tissue to said power supply system for storage of energy in said storage capacitor, said processing system being powered by said power supply system and the energy stored in said storage capacitor.

20. The medical device of claim 15, wherein said communication device includes a transmitter and is operable to transmit data from said processing system to the remote system.

21. The medical device of claim 20, wherein said processing system is operable to sense a voltage between said anode and said cathode as said predetermined functions and transmit a value representative of said sensed voltage to the remote system through said transmitter.

22. The medical device of claim 20, wherein said processing system includes a memory for containing a predetermined ID therein unique to the medical device and said transmitter is operable to transmit said ID to the remote system.

23. The medical device of claim 20, wherein said processing system includes a memory for storing information received from the remote system, said information constituting configuration information for configuring the operation of said processing system, and wherein said processing system is configured in accordance with said stored information.

24. The medical device of claim 15, wherein said semiconductor substrate is spherical in shape.

25. The medical device of claim 24, wherein both said anode and said cathode are fabricated on spherical semiconductor substrates.

26. The medical device of claim 25, wherein said processing system is distributed between said anode and said cathode partially on each of said semiconductor substrates.

27. An implantable medical device for implanting in tissue, comprising:
   an anode for conductively interfacing with the tissue;
   a cathode for conductively interfacing with the tissue;
   at least one of said anode or cathode formed with an integrated circuit on a semiconductor substrate;
   a support structure for supporting said anode and said cathode a predetermined distance apart;
   said semiconductor substrate including a processing system;
   an interconnection network for interconnecting said at least one of said anode or cathode that is formed on said semiconductor substrate to the other thereof, such that said anode and said cathode are interfaced with said processing system, and wherein said anode and said cathode allow said processing system to interface with the tissue to perform predetermined functions in association therewith; and
   a voltage generator operating in conjunction with said processing system to generate a voltage across said anode and said cathode as said predetermined functions.

28. The medical device of claim 27, wherein said processing system is operable to control said voltage generator to generate said voltage for a predetermined duration of time.

29. The medical device of claim 28, wherein said processing system is operable to control said voltage generator to generate said voltage for said predetermined duration of time and at predetermined intervals.

30. The medical device of claim 27 and further including a communication device including a receiver for receiving signals from a separate remote system external to the tissue, said processing system performing said predetermined functions in response to the signals received from the remote system.

31. The medical device of claim 30, and further including a power supply system, said power supply system having associated therewith a storage capacitor, and wherein said communication device is operable to receive an external signal from the remote system for inductively coupling power across the tissue to said power supply system for storage of energy in said storage capacitor, said processing system being powered by said power supply system and the energy stored in said storage capacitor.

32. The medical device of claim 27, wherein said communication device includes a transmitter and is operable to transmit data from said processing system to the remote system.

33. The medical device of claim 32, wherein said processing system is operable to sense a voltage between said anode and said cathode as said predetermined functions and transmit a value representative of said sensed voltage to the remote system through said transmitter.

34. The medical device of claim 32, wherein said processing system includes a memory for containing a predetermined ID therein unique to the medical device and said transmitter is operable to transmit said ID to the remote system.

35. The medical device of claim 27, wherein said predetermined function comprises a pacemaking function, wherein said voltage generator is operable to generate pulses of a predetermined duration and interval to stimulate the tissue, whereby the tissue comprises myocardium.

36. An implantable epicardial electrode for implanting in human myocardium tissue, comprising:
   an anode for conductively interfacing with the myocardium tissue;
   a cathode for conductively interfacing with the myocardium tissue;
   at least one of said anode or cathode formed with an integrated circuit on a semiconductor substrate;
   a support structure for supporting said anode and said cathode a predetermined distance apart;
   said semiconductor substrate including a processing system;
   an interconnection network for interconnecting said at least one of said anode or cathode that is formed on said semiconductor substrate to the other thereof, such that said anode and said cathode are interfaced with said processing system, and wherein said anode and said cathode allow said processing system to interface with the myocardium tissue to perform predetermined functions in association therewith; and
   a voltage generator operating in conjunction with said processing system to generate a voltage across said anode and said cathode, whereby the myocardium tissue is stimulated to a polarized state.

37. The medical device of claim 36, wherein said processing system is operable to control said voltage generator to generate said voltage for a predetermined duration of time.

38. The medical device of claim 37, wherein said voltage is generated for said predetermined period of time and at predetermined intervals.

* * * * *